United States Patent [19]

Otto

[11] 3,993,741
[45] Nov. 23, 1976

[54] $^{75}$SE AND $^{123m}$TE COMPOUNDS FOR FAT RESORPTION TESTS

[75] Inventor: Petrus Philippus Hermann Leonardus Otto, Bleijenburg, Netherlands

[73] Assignee: U.S. Philips Corporation, New York, N.Y.

[22] Filed: Nov. 1, 1974

[21] Appl. No.: 520,033

[30] Foreign Application Priority Data
Nov. 8, 1973  Netherlands ..................... 7315287

[52] U.S. Cl. .............................. 424/1; 23/230 B; 260/607 R
[51] Int. Cl.$^2$ ................. A61K 29/00; A61K 43/00; G01T 1/161; G21H 5/02
[58] Field of Search ............... 23/230 B; 260/607 R; 424/1, 1.5

[56] References Cited
OTHER PUBLICATIONS

Bernard, Chemical Abstracts, vol. 79, 1973, p. 136, item No. 112907p.

Leinbach et al., Chemical Abstracts, vol. 77, 1972, p. 241, item No. 16283v.

Ditchburn et al., International Journal of Applied Radiation and Isotopes, vol. 25, No. 4, Apr. 1974, pp. 167-176.

*Primary Examiner*—Benjamin R. Padgett
*Assistant Examiner*—Christine M. Nucker
*Attorney, Agent, or Firm*—Frank R. Trifari; Norman N. Spain

[57] ABSTRACT

The invention relates to a method of determining the fat resorption, in which a radio-active test fat and reference substance are orally administered. According to the present invention a triether or glycerol of which one or more oxygen atoms are substituted by atoms of the isotope $^{75}$Se or $^{123m}$Te, is used as a reference substance. In a preferred embodiment use is made of $^{125}$I- or $^{131}$I-triolein as test fat. The proposed reference substances are novel compounds. A suitable reference substance is for example 1-butylselenyl-$^{75}$-Se-2,3-dioctadecyloxypropane.

15 Claims, No Drawings

$^{75}$SE AND $^{123m}$TE COMPOUNDS FOR FAT RESORPTION TESTS

The invention relates to a method of determining the fat resorption in man and animal as well to novel substances and preparations derived therefrom which may be employed for this method.

Various methods are known for determining defects in the fat resorption in man and animal. For example, an exact amount of a test fat may be administered to a test person or test animal and it may be subsequently ascertained through a faeces test which part of the administered fat was resorbed in the body. This method is sometimes termed the chemical balance method. Drawbacks of this method are for example the necessity of hospitalization of a test subject and the inaccuracy of the method, because generally the requirement of quantitative collection of the faeces cannot be met. Furthermore, there is no possibility of correction for endogenously produced fat and the method is rather laborious owing to the troublesome extraction and purification of test fat from the faeces.

According to a second method, known as the isotope balance method, a test fat labelled with a radioactive isotope is administered. With this method it is also necessary to collect the faeces quantitatively to be able to ascertain through radioactivity measurements which part of the administered fat is resorbed or not resorbed in the body.

According to still another method, known as the isotope ratio method, a radioactively labelled test fat and a radioactively labelled reference substance, also called a tracer, are administered. The tracer should not be resorbed in the body and should have the same turn-over rate in the gastro-intestinal tract as the non-resorbed portion of the radioactive test fat. Some time after administration of the test fat and tracer it is ascertained through a faeces test to what extent the mutual ratio of the amount of tests and the amount of tracer is modified as a result of the passage through the gastro-intestinal tract.

In the Journal of Lipid Research 11, p. 231–236 (1970) it is stated that with rats good results of fat resorption tests in accordance with the isotope ratio method are attained if $^{14}$C labelled triolein is employed as a test fat and 1-hexadecyl-2,3-bisdodecyl-glycerol labelled with $^3$H is employed as a tracer. By determination of the $^3$H-radioactivity and $^{14}$C-radioactivity both in the test dose and in the collected faeces of one day, the extent to which the mutual ratio of the amount of test fat and the amount of tracer has changed as a result of the passage through the gastro-intestinal tract may be determined. From this the percentage of resorbed test fat is calculated with the aid of the following formula:

$$\% \text{ resorbed } {}^{14}\text{C-triolein} = 100 - \frac{{}^3\text{H}/{}^{14}\text{C (in test dose)}}{{}^3\text{H}/{}^{14}\text{C (in one day's faeces)}} \times 100$$

The use of the previously mentioned isotope ratio method in fat-resorption determination has the following drawbacks. First of all it is still necessary to collect the faeces of at least one day. Furthermore, the faeces thus obtained must be subjected to various chemical and physical processes in order to extract the test fat and the tracer and dissolve them in toluene. The solutions obtained are taken up in a scintillation-counter liquid and subsequently the radioactivity is determined with the aid of a Picker Liquimat liquid-scintillation-counter. All these operations are time-consuming and moreover increase the risk of radioactive contamination of the environment. The radio-isotopes $^{14}$C and $^3$H which are used have long half lives and, moreover, they cannot readily be monitored. This applies in particular to the $^3$H-isotope. It is necessary to take special precautions to prevent radioactive contamination.

Another drawback is that $^{14}$C radioisotope is resorbed through resorption of the test fat in the subject's body. Owing to the long halflife and the complex detection of the $^{14}$C-isotope, such a resorption is considered to be undesirable.

The invention relates to a method of determining the fat resorption in man and animal in accordance with the previously mentioned isotope ratio method, a radioactive test fat as well as a radioactive reference substance being orally administered and radioactivity measurements of the administered substances and of the faeces being performed to ascertain to what extent the ratio between the amount of test fat and reference substance has changed owing to the passage through the gastro-intestinal tract. The invention is characterized in that, as reference substance, a triether of glycerol is employed of which one or more oxygen atoms are substituted by atoms of the radio-isotope $^{75}$Se or $^{123m}$Te.

These triethers of glycerol provided with the isotope $^{75}$Se or $^{123m}$Te are novel compounds. The invention also relates to these novel substances as well as to preparations suitable for oral administration, which contains these substances as an active constituent.

In particular, it has been found that the method according to the invention yields favorable results if as reference substance a glycerol triether according to the invention is employed which complies with the formula

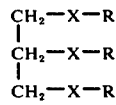

where X represents an oxygen atom, $^{75}$Se-atom or $^{123m}$Te-atom, where at least one of the substituents X represents a $^{75}$Se-atom or $^{123m}$Te-atom, and R signifies a straight or branched alkyl group or aralkyl group with from 2–20 carbon atoms, with the proviso that the R substituents together contain at least 20 carbon atoms. Compounds according to the invention which satisfy the formula

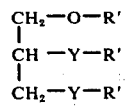

where Y represents an oxygen atom or $^{75}$Se-atom, at least one of the substituents Y being a $^{75}$Se-atom, and R' is a straight or branched alkyl group with from 2 to 20 carbon atoms, the R' substituents, together containing at least 20 carbon atoms, are found to be particularly suited for use as reference substance in the method according to the invention.

Examples of preferred reference substances according to the invention are compounds which satisfy the following formulas:

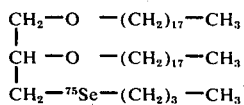

and

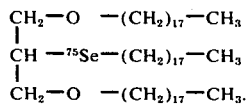

The reference substances according to the invention have a half life which is substantially shorter than that of the tritium labelled reference substance known from the J.Lip.Res. 11, p. 231–236 (1970). Moreover the reference substances (tracers) according to the invention are γ-emitters and as such they can be traced and counted more easily than the known tracer which produces a very soft β-radiation. A possible contamination of the environment with the tracer according to the invention, on account of the short halflife and the easy detection, is far less objectionable than contamination of the environment with the known tracer.

Tests have revealed that the tracer according to the invention is not resorbed in the human or animal body. Within three days upon administration of the tracer, 96–100% of the tracer is recovered in the faeces. The turn-over rate of the tracer in the gastro-intestinal tract is as high as that of the non-resorbed test fat. No separation of tracer and test fat takes place.

Owing to said favorable properties of the tracer according to the invention, the method of determining the fat resorption according to the invention is also favourably compared with for example the method described in J.Lip.Res. 11, p. 231–236.

In a preferred embodiment of the method according to the invention the known test fats $^{125}$I-triolein or $^{131}$I-triolein, i.e. triolein labelled with the radio-isotope $^{131}$I or $^{125}$I, are employed in addition to the previously mentioned tracer. A fat resorption determination in accordance with the preferred method has further advantages compared with a fat resorption determination performed in accordance with J.Lip.Res. 11, p. 231–236.

It has been found, for example, that the ratio between the amount of tracer and test fat in the faeces, in accordance with the preferred method, can be determined by measuring the radio-activity of a faeces sample. For this purpose only a very small amount of faeces is required, whereas in accordance with the known method the radio-activity of the collected faeces of one day has to be measured. Such a faeces sample may be selected by the test subject himself and delivered to the institute for examination. Hospitalization is no longer necessary or desirable. A further advantage is that the radioactivity of the faeces sample can be measured directly with a scintillation counter for γ-radiation, employing for example by an NaI single-crystal or Ge(Li) crystal. Consequently, the faeces need no longer be subjected to various physical and/or chemical extraction processes, as with the known method, but are readily suited for radio-activity measurement. The operations associated with the faeces test are consequently minimized so that the risk of radioactive contamination of the environment is greatly obviated. Moreover, because of the nature of the radiation (γ-radiation) and the short halflives of the radio-isotopes in the tracer and test fat, possible radio-active contamination can easily be detected and also decreases rapidly owing to radio-active decay.

Furthermore, the resorption of the $^{125}$I or $^{131}$I-triolein in the human body is less objectionable, owing to inter alia the short halflife, than the resorption of the $^{14}$C-triolein known from the J.Lip.Res. 11, 1970, p. 231–236.

It is obvious that the faeces sample to be examined is to be selected from those faeces in which the tracer and possibly non-resorbed test fat occur. In order to facilitate such a selection, in a further favourable embodiment of the method according to the invention, a staining material is administered to the test subject, in addition to the tracer and test fat. The staining material is administered simultaneously or substantially simultaneously with the tracer and test fat. Tests have revealed that differently stained faeces, as a result of the administration of a staining material, actually contain tracer and non-resorbed test fat.

The percentage of resorbed test fat and thus the fat-resorption percentage, as previously stated, can be determined by checking to what extent the mutual ratio of the amount of test fat and tracer has changed as a result of the passage through the gastro-intestinal tract. For this purpose the following formula is used:

$$\% \text{ of resorbed test fat} = 100 - \frac{\text{ratio iodine isotope and selenium or tellurium isotope in faeces sample}}{\text{ratio of iodine isotope and selenium or tellurium isotope in test dose}} \times 100$$

The ratio in the test dose is determined with the aid of a sample which is taken from the test dose. The radioactivity measurement of the non-administered test dose sample is conducted simultaneously or substantially simultaneously with the radioactivity measurements of the faeces sample. This ensures that the value of the ratio measured on the test dose sample can be inserted directly in the above formula. Corrections for radioactive decay of the isotopes during the test period are not necessary.

For practical use in fat resorption determinations the tracer according to the invention is processed into a preparation suitable for oral administration. Examples of preparations and preparation forms according to the invention are tablets, capsules, oil solutions and oil dispersions. In all of these preparations the tracer is mixed with a solid or liquid inert carrier material. The tracer according to the invention is preferably dissolved in an inert solvent Suitable solvents are for example, aliphatic hydrocarbons, aromatic hydrocarbons, vegetable, animal and mineral oils. Highly suitable solvents are esters of glycerol, such as for example a mixture of triglycerides of caprylic acid and caproic acid. Such a mixture is available under the trade mark Delios S.

The amount of tracer in the preparations according to the invention is not subject to narrow limits. The upper limit is determined by the maximum permissible dose of radioactivity which may be administered to the patient. The upper limit is defined by the minimum radioactivity dose that can still be determined quantitatively in the test equipment. Generally, satisfactory results will be achieved with preparations in which the amount of tracer radioactivity per gramme of preparation is 0.01 $\mu$Ci to 10 $\mu$Ci.

In a favorable embodiment, the preparations according to the invention contain $^{125}$I or $^{131}$I-triolein in addition to the tracer. Another favourable embodiment furthermore contains a staining material. The amount of $^{125}$I or $^{131}$I-triolein in the preparation may also vary within wide limits. The upper and lower limits of the amount of $^{125}$I or $^{131}$I-triolein are dictated by the same factors as stated previously for the tracer. It is to be borne in mind that the radio-active triolein is to a large extent resorbed in the body and furthermore has a shorter halflife than the isotope employed in the tracer. The lower limit of the amount of $^{131}$I or $^{125}$I triolein to be used is consequently greater than that of the tracer. Satisfactory results are obtained if the amount of $^{131}$I or $^{125}$I triolein used in the preparation according to the invention corresponds to a radioactivity dose of 1–10 $\mu$Ci per gramme of preparation.

Preparations according to the invention which in addition to the tracer also contain $^{131}$I or $^{125}$I triolein and, if desired a staining material, are ready for immediate use. It is obvious that it is extremely convenient for the user if the manufacturer can supply such a ready-for-use product. The stability in storage of such multi-component preparations is determined by the isotope having the shortest halflife such as for example the $^{131}$I-isotope. The halflife of this isotope is 8 days. The $^{75}$Se or $^{123m}$Te isotope used in the tracer has a substantially longer halflife. For example, the halflife of $^{75}$Se is 120 days. A multi-component preparation according to the invention should be used by the test subject within a few days after it has been supplied by the manufacturer. If for some reason this is not possible the preparation can no longer be used. This also means that the tracer which can be kept substantially longer is also lost. In order to avoid such a loss of tracer it is preferred to supply the tracer and test fat, such as $^{131}$I-triolein separately to the user. The user, briefly before use in a fat-resorption determination, must mix the tracer and the test fat and thus prepare the multi-component preparation according to the invention himself. The tracer and the test fat are then supplied in the form of solutions. Suitable solvents are for example the previously stated aliphatic hydrocarbons as well as oils. Preferably, the same solvent such as the previously mentioned mixture of triglycerides of caprylic acid and caproic acid, is used for tracer and the test fat.

The solutions of the tracer and the test fat are supplied in a kit which facilitates the said mixing operation. For example, both the tracer solution and the test fat solution are supplied in flasks or vials provided with a screw cap. Another possibility is to supply the solutions in vials provided with rubber sealing diaphragms. With the aid of an injection syringe, the content of one vial may be readily transferred to the other vial by inserting the needle through the sealing diaphragms. In accordance with yet another embodiment one of the two solutions is supplied in an ampoule whose neck fits the neck portion of a flask or vial which contains the other solution.

A fat resorption determination according to the invention may be performed as follows. For example in a method as described above a solution of the tracer according to the invention is mixed with a $^{125}$I or $^{131}$I-triolein solution. From the mixture a sample is taken and the remainder is administered to the test subject. Administration is preferably effected in combination with a standard meal which for example contains 30 grams of fat. Simultaneously, an ampoule containing a staining material is administered to the patient. The sample is taken from that part of the faeces which, owing to the administration of the staining substance, is coloured differently. The radioactivities of the isotopes present in the faeces sample are measured by placing the sample in a scintillation counter for $\gamma$-radiation. At the same time the radioactivity of the test dose sample is also measured in a scintillation counter for $\gamma$-radiation. The measured values are inserted in the previously stated formula, after which the percentage of $^{125}$I or $^{131}$I-triolein which is resorbed and thus the degree of fat resorption, is calculated.

The tracers or reference substances according to the invention are novel compounds which may be prepared in accordance with methods which are known for synthesizing similar substances, or by methods related thereto.

For example the substances may be prepared by reacting a compound of the formula

where A represents a bromine atom or the group OR, with the proviso that at least one of the substituents A is a bromine atom, and R has the previously stated meaning, in the presence of a solvent and at a low temperature with a compound of the formula

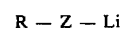

where R has the previously mentioned meaning and Z represents a $^{75}$Se-atom or $^{123m}$Te-atom, yielding a compound of the formula

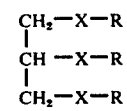

where R and X have the previously stated meanings.

Useful solvents are for example ethers such as dioxane and tetrahydrofuran. A suitable reaction temperature is for example a temperature ranging between +10° C and −20° C.

The above starting material of the formula can be obtained by reacting a compound of the formula $$\begin{array}{l} CH_2-B \\ CH-B \\ CH_2-B \end{array}$$

where B represents an OH-group or an OR-group, with thionylbromide in the presence of a solvent. A suitable solvent is for example dimethylformamide. The reaction temperature varies from room temperature to the boiling point of the employed solvent. The starting material of the formula $$R-Z-Li$$

is prepared by irradiating in a reactor selenium powder or tellurium powder in a solvent, which as a result of this is enriched with 75Se or $^{123m}$Te, a suitable solvent being tetrahydrofuran and subsequently adding the resultant solution, at a lower temperature such as −15° C to a solution of a compound of the formula LiR. In the last mentioned formula R has the previously stated meaning. A suitable solvent for the compound of the formula LiR is for example an aliphatic hydrocarbon such as hexane.

The invention will be described in more detail with reference to the following embodiments.

1. Preparation of 1-butylselenyl-$^{75}$-Se-2,3-dioctadecyloxypropane, which satisfies the formula $$\begin{array}{l} CH_2-O-(CH_2)_{17}-CH_3 \\ CH-O-(CH_2)_{17}-CH_3 \\ CH_2-Se^*-(CH_2)_3-CH_3 \end{array}$$

where Se* represents selenium enriched with $^{75}$Se-isotope.

a. synthesis of 1-bromo-2,3-dioctadecyloxypropane

To a solution of 15 g of 1,2-dioctadecyloxy-2-propanol in 450 ml of dimethylformamide 21 g of thionylbromide were added dropwise while stirring and cooling, after which the reaction mixture was heated at 100° C for 5 hours. After cooling down, the resultant mixture was slowly poured into 400 ml of 5% sodium-bicarbonate solution. The aqueous solution was extracted with 4 × 150 ml of diethylether, after which the ether extract was consecutively washed with water, 5% sodium bicarbonate solution and water. After drying on sodium sulphate the solvent was removed under vacuum. The coarse product thus obtained was purified by means of column chromatography. The yield was 14 g of 1-bromo-2,3-dioctadecyloxypropane with a melting point of 38°–38.8° C.

b. synthesis of lithiumbutylselenide

In a dry oxygen-free argon atmosphere 0.3 ml of 2.3-molar butyl lithium, dissolved in hexane, were added in 10 minutes into a well-stirred suspension of 80 mg of irradiated selenium powder (specific acitivity 1.5 mCi $^{75}$Se per milligramme atom) in 5 ml of tetrahydrofuran at −15° to −10° C. A dark red colour is obtained, which at the end of the reaction changes to colourless. Into the resulting solution of lithium butylselenide some drops of ethanol were injected to decompose the possible excess of butyl lithium; after which the solution without further purification was employed for the next step in the reaction.

c. synthesis of 1-butylselenyl-$^{75}$-Se-2,3-dioctadecyloxypropane

In a dry oxygen-free argon atmosphere a solution of 406 mg 1-bromo-2,3-dioctadecyloxypropane in 4 ml of tetrahydrofuran were added to the solution of b at −10° C.

The temperature of the reaction mixture was raised to 20° C in 4 hours. After being kept at room temperature for 16 hours all volatile constituents were distilled off in vacuum. The yield was 750 μCi of 1-butylselenyl-$^{75}$Se-2,3-dioctadecyloxypropane, having a melting point of 29.1°–30.1° C.

2. Preparation of 2-octadecylselenyl-$^{75}$Se-1,3-dioctadecyloxypropane, which satisfies the formula $$\begin{array}{l} CH_2-O-(CH_2)_{17}-CH_3 \\ CH-Se^*-(CH_2)_{17}-CH_3 \\ CH_2-O-(CH_2)_{17}-CH_3 \end{array}$$

where Se* represents selenium enriched with $^{75}$Se-isotope.

a. synthesis of 1,3-dioctadecyloxy-2-propanol 89 g of 1-octadecanol were added to a solution of sodium methanolate in methanol, obtained from 4.6 g of sodium and 60 g of methanol. While passing dry nitrogen over it, the resultant solution was slowly heated to 160° C and kept at that temperature for 5 hours to remove the methanol. After cooling down the mixture to 100° C, 10.0 g of 1,3-dichloro-2-propanol were added, after which the reaction mixture was kept at 150° C for 2 hours. After cooling down the coarse reaction mixture was repeatedly crystallized from ethanol. The fractions obtained were checked for purity with the aid of thin-layer chromatography. 15.5 g of 1,3-dioctadecyloxy-2-propanol, melting point 62°–64.5° C were obtained.

b. synthesis of 2-bromo-1,3-dioctadecyloxypropane

To a solution of 11.0 g of 1,3-dioctadecyloxy-2-propanol in 400 ml of dry dimethylformamide 20 g of thionyl bromide were added dropwise, while stirring well and boiling, after which the reaction mixture was heated at 100° C for 5 hours. After cooling down said mixture was slowly poured out into 400 ml of 5% sodium bicarbonate solution. The aqueous solution was extracted with 4 × 150 ml of hexane, after which the hexane extract was consecutively washed with water, 5% sodium bicarbonate solution, and water. After drying on sodium sulphate 0 aq the solvent was removed under vacuum. The resulting coarse product was purified by means of column chromatography. After evaporation and drying in vacuum (P = 0.001 mm Hg, t = 40° C) 8 gram were obtained, melting point 47.9° – 48.7° C.

c. synthesis of octadecyl lithium in ether

In a three-necked flask 35 cm of lithium wire of a diameter of 1.5 mm were pressed under an argon atmosphere. After the addition of 15 ml of ether 7.4 g of octadecylbromide were added, while stirring well at −10° C. After the reaction mixture was stirred for another 4 hours at −10° C it was brought at room temperature and filtered through glass wool. The final volume was approximately 65 ml. The solution was stored at −20° C. The content of octadecyllithium was 0.164 mmol per ml of solution.

d. synthesis of 2- octadecylselenyl-$^{75}$Se-1,3-dioctadecyloxypropane.

In a three-necked 50 ml flask 4 ml of 0.16 mol octadecyllithium dissolved in ether were added into a well stirred suspension of 80 mg of irradiated selenium powder (specific activity 2.47 mCi $^{75}$Se per mmol) in 5 ml of tetrahydrofuran at −15° C to −10° C in 15 minutes. Into the resultant solution some drops of ethanol were then added to decompose the possible excess of octadecyllithium, after which a solution of 390 mg of 2-bromo-1,3-dioctadecyloxypropane in 5 ml of tetrahydrofuran were added at −10° C. The temperature of the reaction mixture was raised to 20° C in 4 hours. After standing at room temperature for 16 hours all volatile constituents were distilled off by vacuum. The residue was taken up in 5 ml hexane and purified with the aid of column chromatography. The resulting fractions were tested for purity with the aid of thin-layer chromatography. 2 fractions of 15 ml and subsequently 11 fractions of approximately 65 ml were collected. The third through fifth fractions contained 2-octadecylselenyl-$^{75}$Se-1,3-dioctadecyloxypropane. These fractions were dried by evaporation and the resulting product was identified via the mass spectrum.

3. Fat resorption test conducted on rats, the radioactive substance 1-butylselenyl-$^{75}$Se-2,3-dioctadecyloxypropane being employed as a tracer and the radioactive substance $^{131}$I-triolein as test fat.

During a four-day period a diet rich in fat which contained 10% of olive oil was administered to 5 rats. After a 24-hour fasting period a test dose was administered consisting of a solution of the above-mentioned tracer and test fat in olive oil. The test dose was obtained by mixing separate olive oil suspensions of test fat and of tracer. A small part of the resulting mixture (sample) was retained for subsequent radio-activity measurements; the remainder of the mixture was administered as test dose. The faeces were collected at the following instants after administration of the test dose: 6, 12, 24, 48 and 72 hours. The radio-activity of the amounts of tracer and test fat contained in the collected faeces was determined in a scintillation counter for γ-radiation. Simultaneously the radio-activity of the amounts of tracer and test fat contained in the samples were also measured. The percentage of resorbed test fat was calculated in two manners:

1. Isotope balance method in accordance with the formula:

$$\% \ ^{131}\text{I-triolein absorption} = 100 - \frac{\text{total } ^{131}\text{I-triolein excretion}}{\text{administered dose of } ^{131}\text{I-triolein}} \times 100.$$

2. Isotope-ratio method in accordance with the formula:

$$\% \ ^{131}\text{I-triolein absorption:} \ 100 - \frac{\text{ratio } ^{131}\text{I}/^{75}\text{Se (in faeces)}}{\text{ratio } ^{131}\text{I}/^{75}\text{Se (in test dose sample)}} \times 100.$$

The isotope ratio method is applied in the period from 6 to 48 hours after administering the test dose. In said period more than 90% of the administered tracer was excreted. For the calculation of the fat resorption percentage in accordance with the isotope balance method the total amount of faeces was used which were excreted in a period 27 hours after administration of the test dose.

The results of the calculation are given in the following table.

| | fat resorption percentage | | | |
|---|---|---|---|---|
| | Isotope balance method | Isotope ratio method | | |
| Rat No. | 0–72 hours | 6–12 hours | 12–24 hours | 24–48 hours |
| 1 | 94.7 | 93.9 | 95.5 | 93.5 |
| 2 | 97.7 | 97.9 | 97.3 | 95.7 |
| 3 | 94.6 | 93.1 | 97.2 | 96.1 |
| 4 | 97.1 | 97.1 | 98.0 | 96.0 |
| 5 | 97.1 | 97.4 | 97.8 | 95.0 |

From this data the conclusion may be drawn that the ratio test-fat/tracer in the faeces is substantially constant throughout the period. This means that with the aid of isotope-ratio method applied the resorption percentage of the test fat may be calculated from an arbitrary faeces sample. In the period between 6 and 12 hours after administering the test dose, approximately 70% of the tracer was excreted. Especially the results obtained in said period by means of the isotope-ratio method exhibit an excellent correlation with the isotope balance method.

4. Fat resorption test conducted on rats employing 1-butylselenyl-$^{75}$Se-2,3-dioctadecyloxypropane as tracer and $^{131}$I-oleic acid as test fat.

A group of 4 rats was prepared for a fat-resorption experiment in the same manner as described in example 3, by administering the rats a high-fat diet during 4 days and subsequently observing a fasting period of 24 hours.

The object of the preparation procedure is to optimize the possibility of fat resorption. Subsequently a test dose was administered which consisted of a solution of the said tracer and test fat on olive oil. The test dose was obtained by mixing separate solutions of the tracer and test fat in olive oil. A part of said mixture was retained for conducting radio-activity measurements at a later instant; the remainder of the mixture was administered as test dose.

A second group of 3 rats were not prepared by means of a high-fat diet and fasting. These rats were also administered a test dose as previously described.

Of both groups of rats the faeces were collected at the following instants after administration of the test dose: 6, 8, 10, 12, 14, 16, 18, 20, 22, 24, 26, 30; 48 and 72 hours. The radio-activity of the tracer and test fat present in the collected faeces was determined with the aid of a scintillation counter for $\gamma$-radiation. Moreover simultaneously the radio-activity of the retained part of the test dose was measured in order to determine the ratio of the radio-activity of the test fat and of the tracer therein. The percentage of resorbed test fat was determined in accordance with the isotope-balance method and the isotope ratio method using the formulas given in example 3.

The isotope ratio method was applied in the period from 0 to 24 hours after the administration of the test dose. In said period 90% of the tracer was excreted.

The isotope balance method was applied to the total amount of excretion in a 78 hour period after the administration of the test dose. The results are specified in the following table.

| | amount of excreted tracer expressed as percentage of administered amount of tracer | | | | | |
|---|---|---|---|---|---|---|
| | patient 1 | | patient 2 | | patient 3 | |
| day | faeces | urine | faeces | urine | faeces | urine |
| 1 | 92.09 | 0.02 | 0.00 | 0.04 | 0.10 | 0.09 |
| 2 | 7.80 | 0.01 | 54.94 | 0.04 | 46.65 | 0.03 |
| 3 | 0.02 | 0.00 | 44.06 | 0.01 | 49.87 | 0.00 |
| 4 | 0.04 | 0.00 | 1.09 | 0.00 | 0.81 | 0.02 |
| 5 | 0.06 | 0.00 | 0.07 | 0.01 | 0.13 | 0.02 |
| total | 100.01 | 0.03 | 100.16 | 0.10 | 97.43 | 0.16 |
| | 100.04 | | 100.26 | | 97.59 | |

B. Fat resorption test on man, using 1-butylselenyl-$^{75}$-Se-2,3-dioctadecyloxypropane as tracer and $^{131}$I-triolein as test fat.

| | Fat resorption percentage | | | | |
|---|---|---|---|---|---|
| | Isotope balance method | Isotope ratio method | | | |
| Rat no. | 0–72 hours | 0–6 hours | 6–8 hours | 8–10 hours | 10–12 hours |
| A 1 | 91.7 | 88.3 | 91.1 | 91.6 | 92.6 |
| 2 | 95.2 | — | 95.1 | 95.3 | 95.6 |
| 3 | 94.5 | — | 94.6 | 94.9 | 94.6 |
| 4 | 89.4 | 86.2 | 89.1 | 90.0 | 90.2 |
| B 1 | 83.4 | 57.4 | 67.2 | 82.2 | 86.4 |
| 2 | 68.1 | 50.0 | 75.4 | 77.4 | 78.0 |
| 3 | 64.2 | 30.3 | 47.9 | 68.0 | 74.0 |

| | Fat resorption percentage | | | | | |
|---|---|---|---|---|---|---|
| | Isotope ratio method | | | | | |
| Rat no. | 12–14 hours | 14–16 hours | 16–18 hours | 18–20 hours | 20–22 hours | 22–24 hours |
| A 1 | — | 93.2 | 92.8 | 93.0 | 93.5 | 94.1 |
| 2 | 95.2 | 96.0 | 93.5 | 95.1 | — | 95.7 |
| 3 | 94.7 | 94.7 | 94.9 | 94.8 | 94.7 | 94.1 |
| 4 | 91.0 | 91.4 | 90.9 | 91.7 | 91.4 | 91.3 |
| B 1 | 86.8 | 86.9 | 87.2 | 87.3 | 87.7 | — |
| 2 | 78.2 | 80.1 | 79.9 | 81.0 | 81.9 | 79.1 |
| 3 | 75.5 | 72.0 | 70.1 | 71.7 | 74.7 | — |

The rats of group A have been prepared with a high-fat diet for 4 days followed by 24 hours fasting.

The rats of group B have not been prepared.

From these results the conclusion may be drawn that generally speaking an increasing percentage of the consecutive fractions of the test fat which pass through the gastro-intestinal tract is resorbed. This is particularly apparent with rats of which the fat resorption is not optimum (group B).

5. Fat resorption test on man.

A. Excretion of the tracer 1-butylselenyl-$^{75}$-Se-2,3-dioctadecyloxy-propane.

Under nursing conditions in which a complete collection of faeces and urine is possible, three patients were administered a capsule containing 1 $\mu$Ci 1-butylselenyl-$^{75}$Se-2,3-dioctadecyloxypropane (tracer) and 10 mg of inactive 1-butylselenyl-2,3-dioctadecyloxypropane, dissolved in 0.4 ml of olive oil. Faeces and urine were collected during 5 days and measured in a Tabor large sample counter. The measured amount of 1-butylselenyl-$^{75}$-Se-2,3-dioctadecyloxypropane (tracer) as a percentage of the administered amount of said radio-active substance is specified in the following table.

Test subjects:

The test was conducted with 3 groups of patients, namely:

a. a test group consisting of test subjects without anammestic indications of steatorrhoea.

b. a group of patients with diarrhoea complaints without chemically demonstrable steatorrhoea.

c. a group of patients with chemically demonstrated steatorrhoea.

Test method

To a mixture of 1-butylselenyl-Se$^{75}$-2,3-dioctadecyloxypropane, inactive 1-butylselenyl-2,3-dioctadecyloxypropane and $^{131}$I-triolein olive oil was added and the mixture was heated to a temperature of 40° C while stirring. The amounts of said substances had been selected so that the resulting solution per ml contained 2.5 $\mu$Ci of 1-butylselenyl-Se$^{75}$-2,3-dioctadecyloxypropane, 25 mg of 1-butylselenyl-2,3-dioctadecyloxypropane and 12.5 $\mu$Ci of $^{131}$I-triolein.

Ampoules were filled with 0.4 ml of said solution. The part of the solution not contained in the ampoules was kept for subsequent radio-activity measurements (test dose sample).

Each patient was administered an ampoule as stated above together with a meal which contained 30 grammes of fat. Simultaneously with the meal a capsule of 250 mg of carmine red (in 2 cases 200 mg of brilliant blue) was taken.

During the subsequent 5-day period, after defecation, a faeces sample was taken preferably from the part of the faeces which was coloured differently owing to the administration of the staining substances. The faeces samples were measured in a Tabor large sample counter, the ratio between the $^{75}$Se-activity of the tracer and the $^{131}$I-activity of the test fat being determined. Simultaneously the above stated test dose sample was measured and the ratio of $^{75}$Se-activity and $^{131}$I-activity therein calculated. With the aid of the formula for the isotope ratio method given in example 3, the fat resorption percentage was calculated from the data thus obtained. Furthermore, the total amount of tracer excreted during the test period was determined. In most cases in which the excreted amount of tracer was more than 90% of the administered amount of tracer, a fat resorption determination in accordance with the chemical balance method was also conducted. For this the collected amount of faeces of the entire test period (5 days) were examined in accordance with chemical balance method as described in the Journal of Biological Chemistry 177, p. 347 (1949). Results:

The results of the examination are specified in the following table.

| Patient | | fat resorption percentage | | | | | chemical balance method | percentage of tracer excreted |
|---|---|---|---|---|---|---|---|---|
| | isotope ratio method according to invention | | | | | | | |
| | day 1 | day 2 | day 3 | day 4 | day 5 | total | | |
| A 1 | | 100.0 | 99.5 | 99.4 | | 99.5 | 98 | 95.4 |
| | | 99.5 | 98.9 | | | | | |
| 2 | | 99.0 | | | | 98.9 | 99 | 99.9 |
| 3 | | 99.6 | 99.5 | 99.0 | | 99.5 | 96 | 94.2 |
| 4 | | | | | 97.5 | 97.5 | 98 | 93.0 |
| 5 | | 97.4 | 100.0 | | 100.0 | 99.3 | 99 | 90.6 |
| 6 | | 98.3 | | 98.8 | 99.3 | 98.9 | 95 | 95.8 |
| 7 | 98.5 | 97.7 | | | | 97.9 | 97 | 96.1 |
| 8 | | 98.8 | | 99.2 | | 99.0 | | 97.4 |
| 9 | 100.0 | 99.9 | | 100.0 | 99.8 | 99.9 | | 99.0 |
| 10 | | | 97.6 | 97.9 | | 97.7 | | 35.3 |
| 11 | | 99.1 | 97.7 | | | 98.4 | | 39.5 |
| 12 | | | | | 99.3 | 99.2 | | 15.9 |
| 13 | | | | | 99.5 | 99.3 | | 38.3 |
| 14 | | | 98.5 | | | 98.5 | | 5.5 |
| 15 | | | 99.4 | | | 99.4 | | 43.4 |
| 16 | | 99.2 | 99.1 | | | 99.0 | | 43.9 |
| 17 | | | 98.8 | | | 98.8 | | 14.8 |
| 18 | | 99.0 | 98.9 | 99.5 | | 99.0 | | 76.2 |
| 19 | 99.5 | 98.7 | 97.8 | | | 99.0 | | 84.4 |
| 20 | | | 100.0 | 99.9 | 98.0 | 99.4 | | 82.4 |
| | | | | | 98.3 | | | |
| 21 | | 99.7 | | | | 99.5 | | 31.9 |
| 22 | | | | 99.4 | | 98.8 | | 40.5 |
| 23 | | | | | 99.2 | 98.6 | | 8.5 |
| 24 | | 96.7 | | | | 96.7 | | 4.8 |
| B 1 | 98.3 | 98.2 | 99.2 | | | 98.5 | 97 | 92.2 |
| 2 | 99.5 | 99.6 | | | | 98.9 | 97 | 91.5 |
| 3 | | 99.6 | | | | 99.1 | | 54.3 |
| 4 | | 99.1 | | | | 98.9 | | 34.8 |
| 5 | 98.1 | 99.0 | | | | 98.6 | | 83.9 |
| | 98.5 | 98.7 | | | | | | |

| Patient | | Fat resorption percentage | | | | | chemical balance method | percentage of tracer excreted |
|---|---|---|---|---|---|---|---|---|
| | isotope ratio method according to invention | | | | | | | |
| | day 1 | day 2 | day 3 | day 4 | day 5 | total | | |
| C 1 | | | | 73.8 | 74.3 | 73.6 | 65 | 104.4 |
| 2 | | | | 47.9 | 45.9 | 47.3 | 64 | 90.9 |
| | | | | 44.9 | 45.6 | | | |
| 3 | | 69.5 | 69.8 | | | 70.1 | | 85.0 |
| | | | 73.6 | | | | | |
| 4 | 63.6 | 62.6 | | | | 64.9 | | 90.5 |
| | 64.8 | 65.3 | | | | | | |
| | 64.2 | 66.5 | | | | | | |
| | | 67.4 | | | | | | |
| 5 | | 12.3 | 23.9 | | | 14.7 | | 61.7 |
| | | 14.3 | 24.1 | | | | | |
| 6 | | 84.3 | | | | 84.1 | | 87.6 |
| 7 | | 86.1 | 93.5 | | | 86.4 | | 86.3 |
| | | 86.1 | | | | | | |
| 8 | 87.3 | | | | | 84.8 | | 79.1 |
| | 87.6 | | | | | | | |
| | 74.9 | | | | | | | |
| | 77.6 | | | | | | | |
| 10 | | 94.9 | | | | 94.6 | | 20.6 |

Notes:
Group A is the test group. Patients of group B suffer from diarrhoea, but not from steatorrhoea. Patients of group C suffer from steatorrhoea.

On the test subjects an average absorption coefficient was found of 98.8% in accordance with the isotope ratio method. As normal range ± 2 S.D. was taken, which normally yields a lower limit of 97.3%.

The group of patients suffering from diarrhoea without chemically demonstrable steatorrhoea also falls within the normal limits. The patients with steatorrhoea have an absorption coefficient of less than 97%. The faeces samples, in which the staining substance is clearly visible, comparatively contain the highest radioactivity, so that accurate measurements are guaranteed.

Comparison of the fat absorption percentages of the isotope ratio method and those of the chemical balance method reveals that a normal result of the chemical balance method always corresponds to a normal result of the isotope ratio test. In the event of serious degrees of steatorrhoea there is no proper accord between the results of the chemical balance method and the isotope ratio test according to the invention.

The faecal yield of the tracer (last column of table) reveals that in the clinic quantative faeces collection is achieved in only a part of the cases, so that the practical value of the chemical balance method in normal clinical examination is to be seriously doubted.

What is claimed is:

1. A compound of the formula

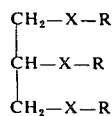

where X is an oxygen atom, $^{75}$Se-atom or $^{123m}$Te-atom, with the proviso that at least one of the substituents X represents a $^{75}$Se-atom or $^{123m}$Te-atom, and R is a straight or branched alkyl group or aralkyl group having from 2 to 20 carbon atoms, all the substituents designated by R together containing at least 20 carbon atoms.

2. A compound of the formula

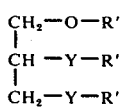

where Y represents an oxygen atom or $^{75}$Se-atom, at least one of the substituents Y being a $^{75}$Se-atom, and R' is a straight or branched alkyl group with from 2 to 20 carbon atoms, all the substituents designated by R together containing at least 20 carbon atoms.

3. A compound of the formula

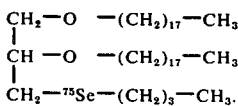

4. A compound of the formula

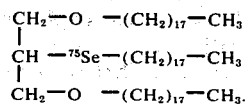

5. A method of preparing a compound of claim 1 comprising reacting, at a low temperature and in a solvent, a compound of the formula

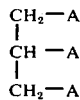

wherein A is bromo or the group OR when R has its previously designated meaning with the proviso that at least one of the substituents designated by A is bromo, with a compound of the formula R — Z — Li wherein R has its previously designated meaning and Z is a $^{75}$Se atom or a $^{123m}$Te atom.

6. A diagnostic preparation suitable for use in fat resorption testing said preparation comprising the compound of claim 1 as a radioactive tracer and an inert solid or liquid carrier therefor.

7. The diagnostic preparation of claim 6 wherein the amount of radioactive tracer present corresponds to a radioactivity of 0.01 μ Ci to 10 μ Ci per gram.

8. A preparation as claimed in claim 6, characterized in that the preparation comprises a compound of the formula

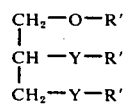

where Y represents an oxygen atom or $^{75}$Se-atom, at least one of the substituents Y being a $^{75}$Se-atom, and R' is a straight or branched alkyl group of from 2 to 20 carbon atoms, all the substituents designated by R together comprising at least 20 carbon atoms, as the tracer.

9. A preparation as claimed in claim 6, characterized in that the preparation contains a compound of the formula

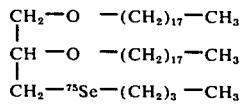

as the tracer.

10. A preparation as claimed in claim 6, characterized in that the preparation comprises a compound of the formula

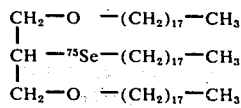

as the tracer.

11. A preparation as claimed in claim 6, characterized in that the preparation also contains $^{125}$I-triolein or $^{131}$I-triolein as a test fat.

12. The diagnostic preparation of claim 11 wherein the amount of $^{131}$I-triolein or $^{125}$I-triolein present corresponds to a radioactivity of 1–10 μ Ci per gram.

13. A preparation as claimed in claim 11, characterized in that the preparation also contains a staining substance.

14. A method of determining the fat resorption in a mammal said method comprising orally administering to said mammal the diagnostic preparation of claim 6 in an amount corresponding to a radioactivity of 0.–1 μ Ci to 10 μ Ci and a radioactively labelled test fat and determining by radioactivity measurements of said orally administered substances and the resultant faeces the change in the ratio between the amount of test fat and radioactive tracer as a result of the passage through the gastro-intestinal tract of said mammal.

15. A method as claimed in claim 12, characterized in that as the radioactively labelled test fat $^{125}$I-triolein or $^{131}$I-triolein is used, in an amount which corresponds to a radioactivity of 1–10 μCi.

* * * * *